US011969530B2

(12) United States Patent
Taguchi et al.

(10) Patent No.: US 11,969,530 B2
(45) Date of Patent: Apr. 30, 2024

(54) BLOOD PURIFICATION SYSTEM AND SOLUTION-PREPARATION-DETERMINING APPARATUS

(71) Applicant: Nikkiso Company Limited, Tokyo (JP)

(72) Inventors: Shunsuke Taguchi, Shizuoka (JP);
Ryouhei Matsumoto, Shizuoka (JP);
Yutaka Ishikawa, Shizuoka (JP);
Takeshi Ichikawa, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 430 days.

(21) Appl. No.: 17/522,246

(22) Filed: Nov. 9, 2021

(65) Prior Publication Data

US 2022/0062519 A1 Mar. 3, 2022

Related U.S. Application Data

(63) Continuation of application No. PCT/JP2020/023853, filed on Jun. 17, 2020.

(30) Foreign Application Priority Data

Jun. 26, 2019 (JP) ................................ 2019-119102

(51) Int. Cl.
*A61M 1/16* (2006.01)

(52) U.S. Cl.
CPC ........ *A61M 1/1656* (2013.01); *A61M 1/1603* (2014.02); *A61M 1/1605* (2014.02);
(Continued)

(58) Field of Classification Search
CPC ............... A61M 1/1603; A61M 1/1605; A61M 1/1621; A61M 1/1656; A61M 1/1657;
(Continued)

(56) References Cited

FOREIGN PATENT DOCUMENTS

JP 2007-236532 A 9/2007
JP 2008-220784 A 9/2008
(Continued)

OTHER PUBLICATIONS

English translation of Japanese Patent Application No. 2012-249746A (2012).*
(Continued)

*Primary Examiner* — John Kim
(74) *Attorney, Agent, or Firm* — Young Basile Hanlon & MacFarlane, P.C.

(57) ABSTRACT

A system and a solution-preparation-determining apparatus which determines whether additional preparation of an undiluted dialysate solution is necessary. A blood purification system includes a solution-preparing unit that prepares an undiluted dialysate solution, a dialysate-supplying unit that prepares a working dialysate at a predetermined concentration by diluting the undiluted dialysate solution received from the solution-preparing unit, a blood-purification-treatment section that includes a blood-purification-apparatus group including at least one blood purification apparatus that performs blood purification treatment in which the working dialysate is supplied to the blood-purification-apparatus group, and a determining unit that determines whether additional preparation of the undiluted dialysate solution is necessary from a result of comparison between an estimated number of treatment sessions expected to be performed by the blood-purification-apparatus group throughout a predetermined period and an actual number of treatment sessions performed by the blood-purification-apparatus group as of a time point during the predetermined period.

12 Claims, 6 Drawing Sheets

(52) U.S. Cl.
CPC ........ *A61M 1/1621* (2014.02); *A61M 1/1657* (2022.05); *A61M 1/1666* (2014.02); *A61M 2202/0413* (2013.01); *A61M 2205/3334* (2013.01); *A61M 2205/3389* (2013.01); *A61M 2205/84* (2013.01)

(58) Field of Classification Search
CPC ........ A61M 1/1666; A61M 2202/0413; A61M 2205/3334; A61M 2205/3389; A61M 2205/84; A61M 2202/0021
See application file for complete search history.

(56) References Cited

FOREIGN PATENT DOCUMENTS

| | | |
|---|---|---|
| JP | 2012-249746 A | 12/2012 |
| JP | 2012-249751 A | 12/2012 |
| JP | 2018-153557 A | 10/2018 |
| WO | 2006/074429 A1 | 7/2006 |

OTHER PUBLICATIONS

International Search Report for Application No. PCT/JP2020/023853, dated Aug. 25, 2020, 4 pgs.

* cited by examiner

[Fig. 1]
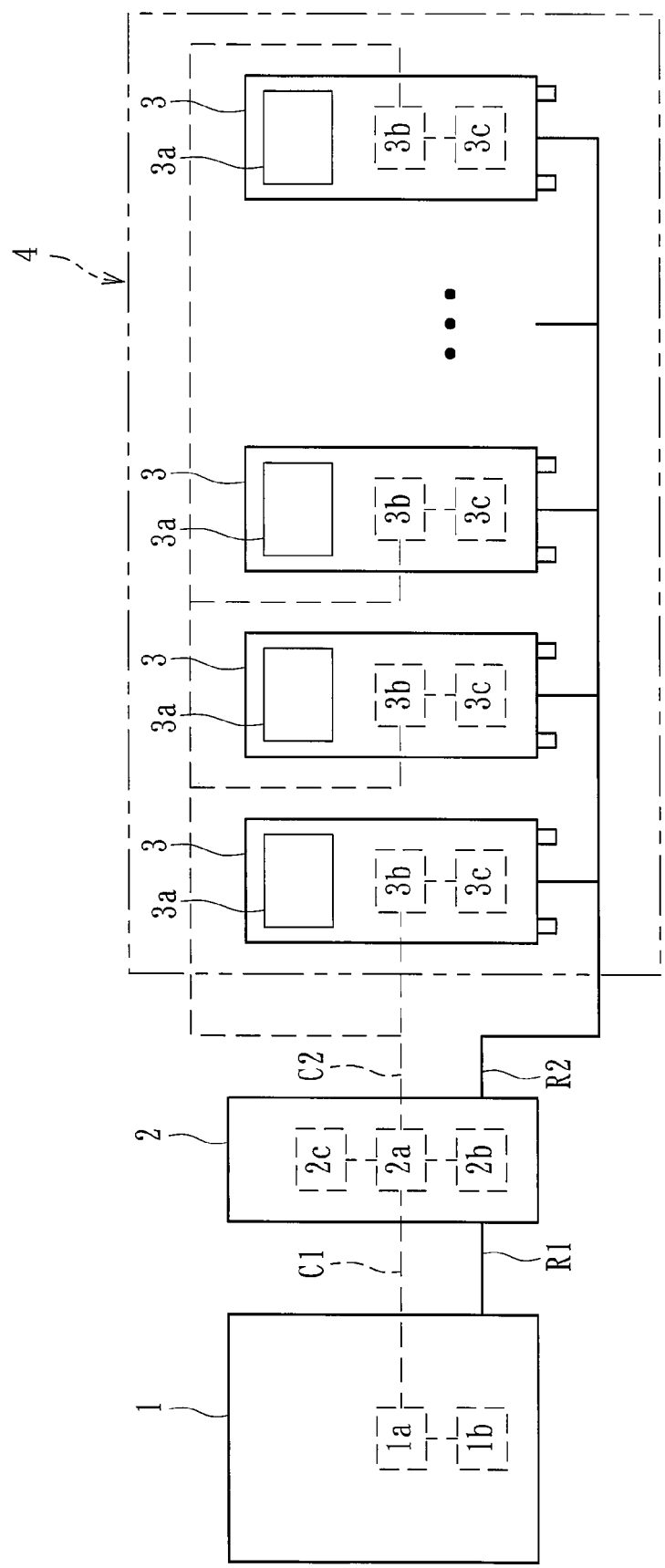

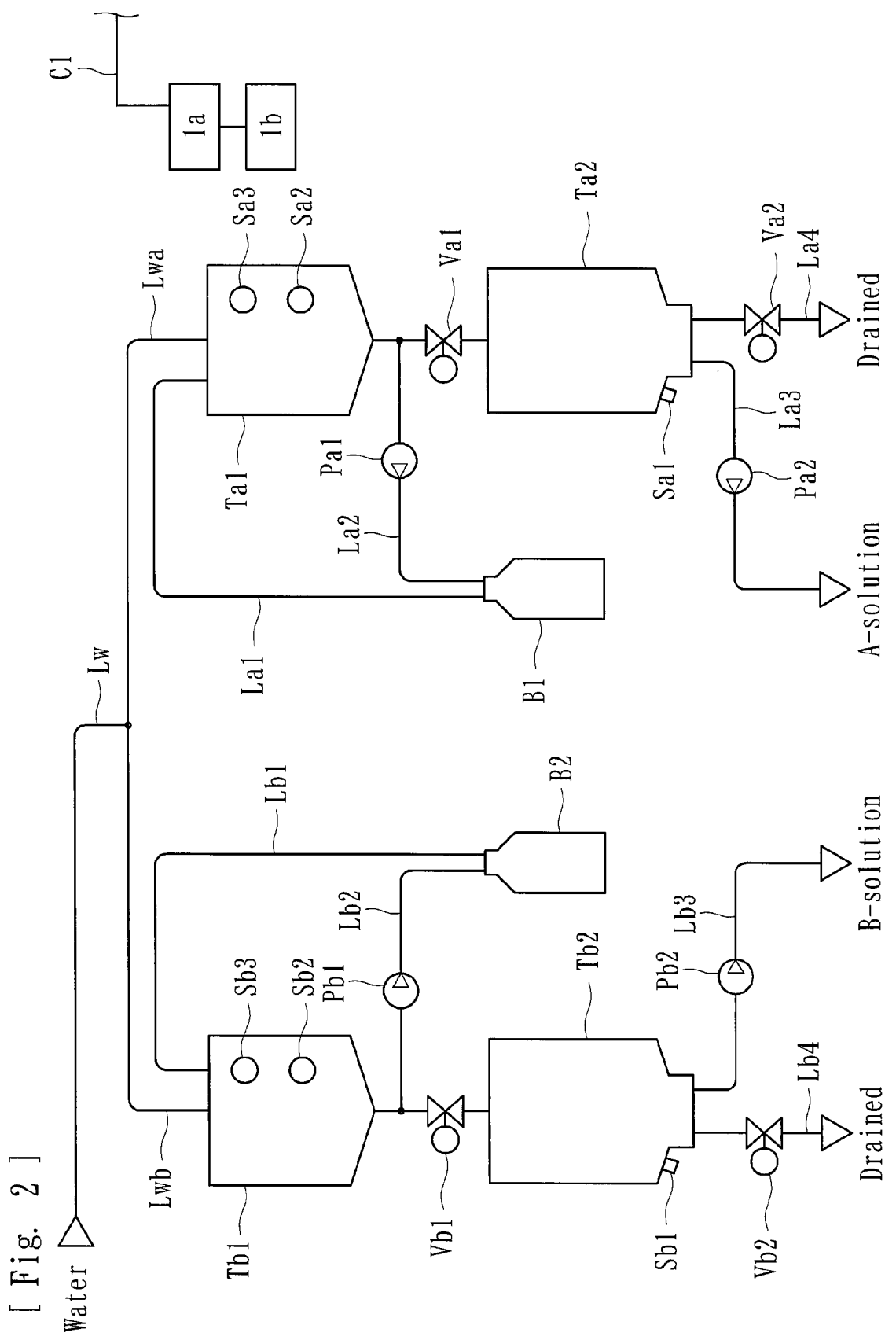
[Fig. 2]

[Fig. 3]
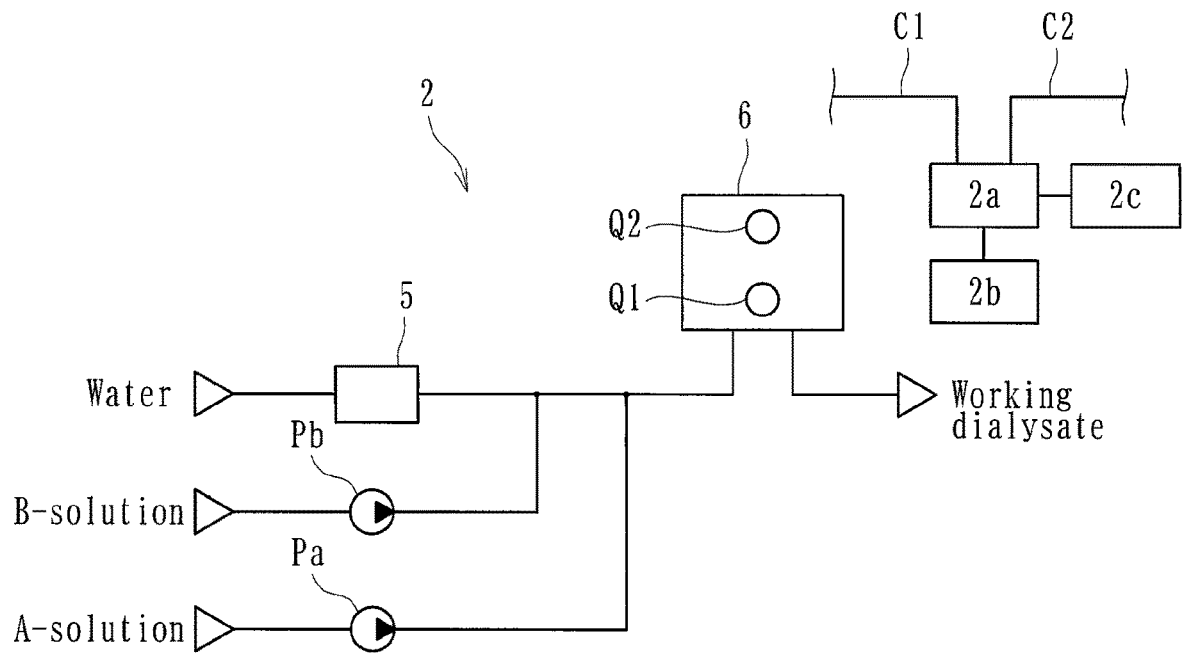
[Fig. 4]
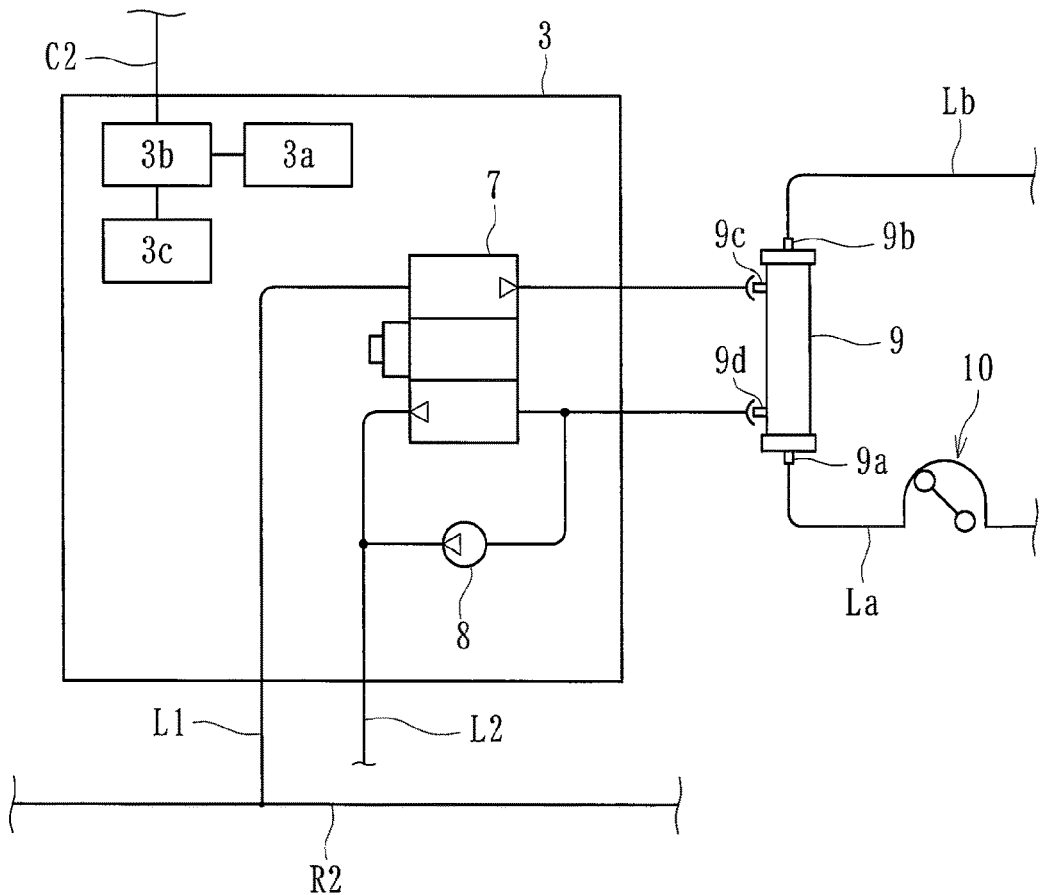

[ Fig. 5 ]
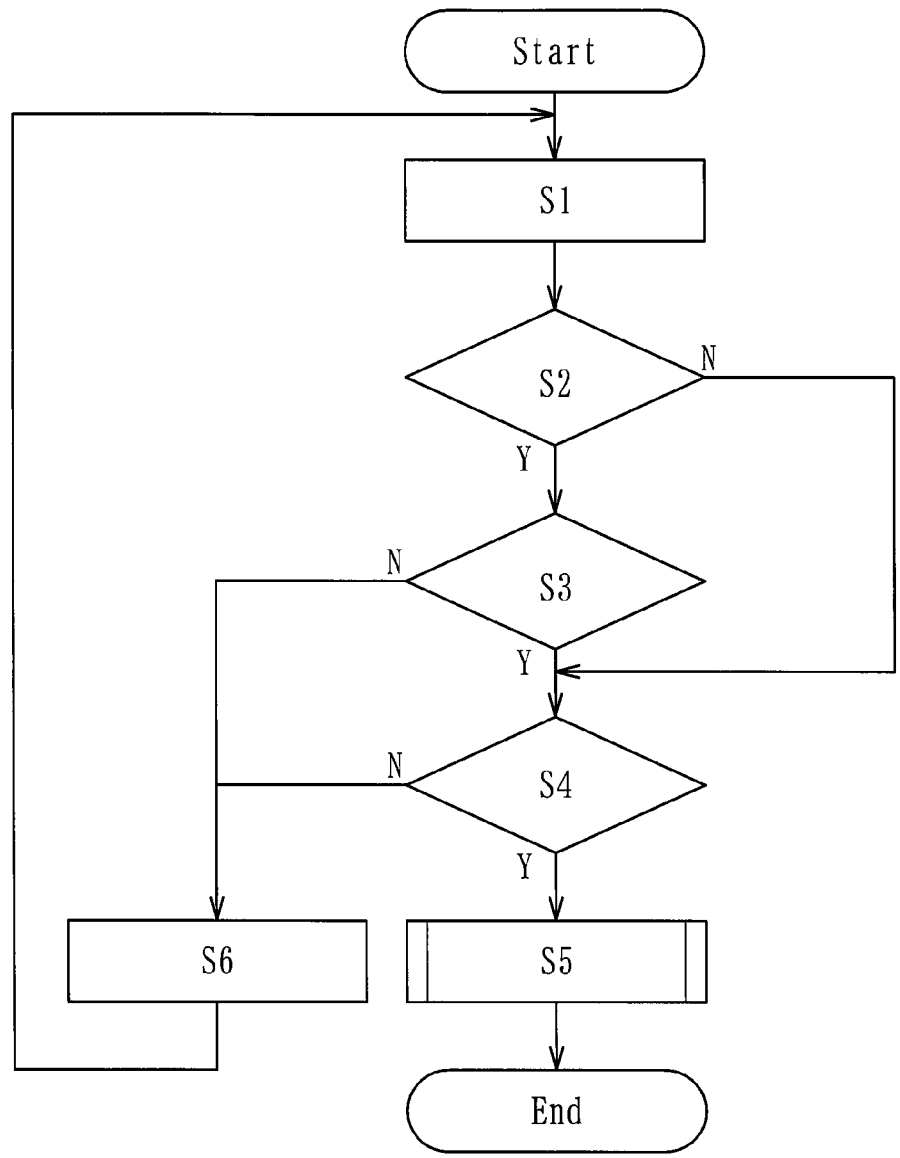
S1  Select one of solutions
S2: Is volume of remaining solution enough?
S3: Is additional preparation necessary?
S4: Ready for additional preparation?
S5: Additional preparation
S6: Stand by

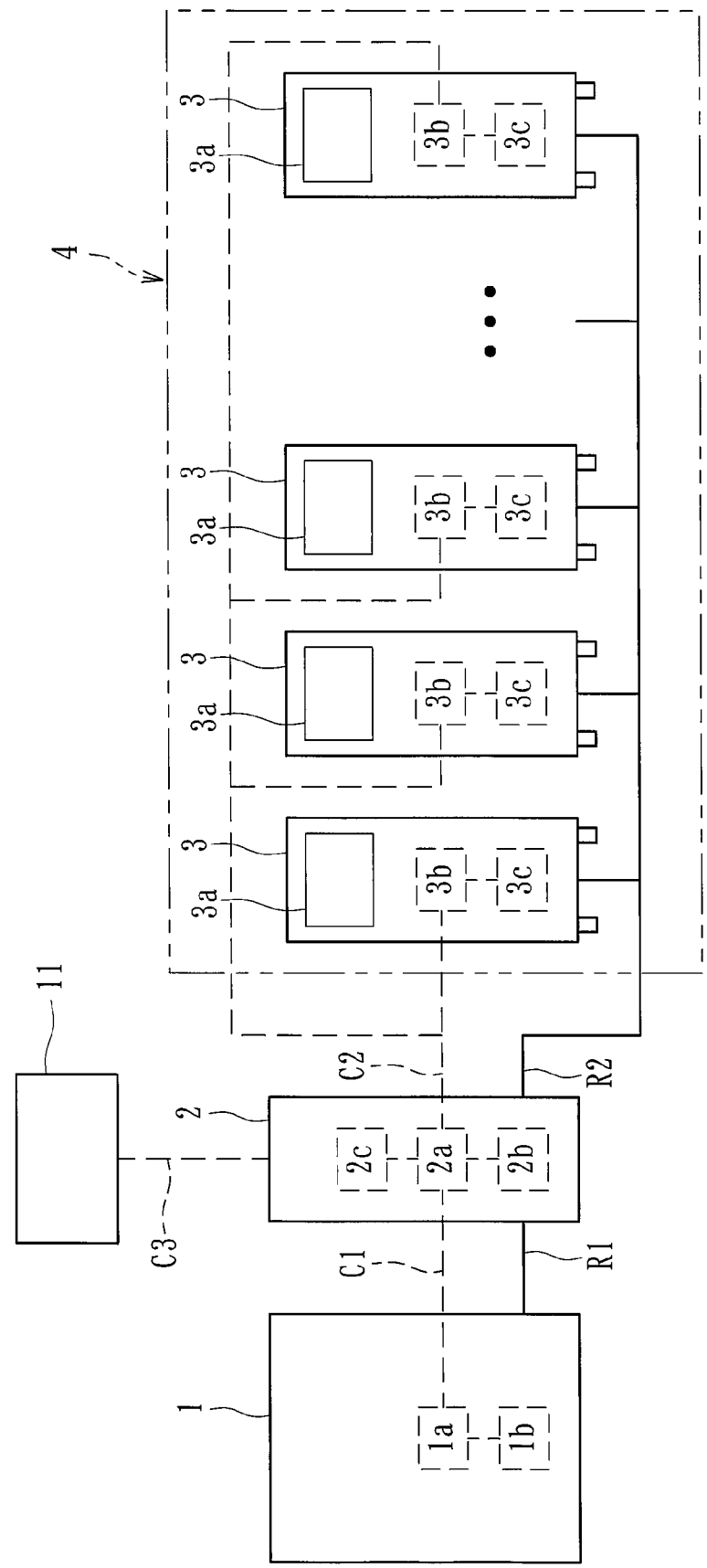
[Fig. 6]

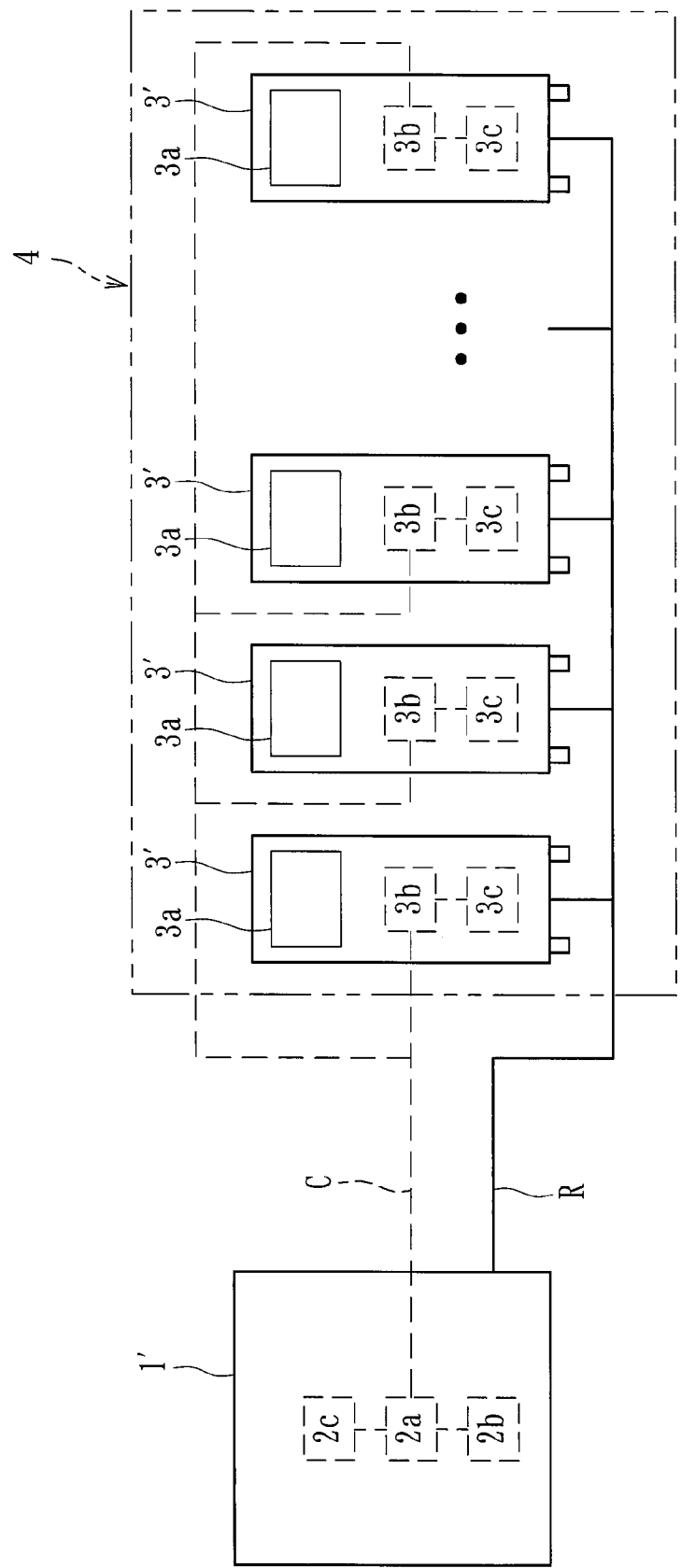
[Fig. 7]

BLOOD PURIFICATION SYSTEM AND SOLUTION-PREPARATION-DETERMINING APPARATUS

CROSS-REFERENCE TO RELATED APPLICATION(S)

This application is a continuation of International Application No. PCT/JP2020/023853 filed on Jun. 17, 2020, which claims priority to Japanese Application No. 2019-119102, filed on Jun. 26, 2019, the entire disclosures of which are hereby incorporated by reference.

FIELD

The present teachings relate to a blood purification system including a solution-preparing unit that prepares an undiluted dialysate solution, a dialysate-supplying unit that prepares a working dialysate at a predetermined concentration by diluting the undiluted dialysate solution received from the solution-preparing unit, and a blood-purification-treatment section that includes a blood-purification-apparatus group including at least one blood purification apparatus for giving blood purification treatment in which the working dialysate prepared by the dialysate-supplying unit is supplied to the blood-purification-treatment group. The present invention also relates to a solution-preparation-determining apparatus.

BACKGROUND

In general, a blood purification system includes a dissolving apparatus and a dialysate-supplying apparatus that are installed in a machine room provided in a medical site such as a hospital, and dialysis monitor apparatuses (blood purification apparatuses) that are installed in a dialysis room (a treatment room) provided at a location different from the machine room. The dialysate-supplying apparatus is connected to each of the dialysis monitor apparatuses with tubes. The dialysate-supplying apparatus prepares a working dialysate at a predetermined concentration by diluting an undiluted dialysate solution prepared by the dissolving apparatus. The number of dialysis monitor apparatuses corresponds to the number of blood purifiers (dialyzers), with which dialysis treatment is given to patients. The working dialysate prepared by the dialysate-supplying apparatus is supplied to the blood purifiers through the tubes.

That is, the working dialysate is distributed from the dialysate-supplying apparatus installed in the machine room to the plurality of dialysis monitor apparatuses installed in the dialysis room and is supplied to the respective dialyzers of the dialysis monitor apparatuses. Such a blood purification system in which dialysis treatment is performed with a working dialysate prepared by a dialysate-supplying apparatus and distributed to individual dialysis monitor apparatuses is typically called "dialysis-treatment central system".

Attempts have been made to provide a blood purification system in which information on the volume of working dialysate to be used (for example, pieces of information such as the volume, flow velocity, hour of supply, and time of supply of the dialysate) is acquired from each of dialysis monitor apparatuses, the volume of the working dialysate to be used in each of the dialysis monitor apparatuses is determined, and the volume of the working dialysate to be used and the volume of an undiluted dialysate solution prepared by a dissolving apparatus (the volume of preparation) are compared. In the known blood purification system, whether any shortage of the undiluted dialysate solution prepared by the dissolving apparatus is expected to occur during the current treatment session is determined. If it is determined that a shortage is expected to occur, an instruction signal is transmitted to the dissolving apparatus, whereby the undiluted dialysate solution of a volume corresponding to the shortage is prepared.

PTL 1: Japanese Unexamined Patent Application Publication No. 2012-249746 the teachings of which is expressly incorporated by reference herein for all purposes.

SUMMARY

The above known blood purification system, however, involves the following problem.

In some medical sites such as hospitals, dialysis treatment is given to a plurality of patients in every treatment hour called "course" (a specific treatment hour that is predetermined). For example, there may be a morning course, an afternoon course, and a night course in a day. In such a case, patients individually visit the treatment room at around the start time of any of the courses that are predetermined for them, and dialysis treatment is given to a plurality of patients at a time.

In such a case, even if it is determined with the application of the known technique that the volume of the undiluted dialysate solution prepared by the dissolving apparatus (the volume of preparation) is enough for the treatment session that is in progress in one specific course, a shortage of the undiluted dialysate solution may occur if there are any courses remaining on that day. Conversely, if it is determined that the volume of the undiluted dialysate solution prepared by the dissolving apparatus (the volume of preparation) is short for the current treatment session, the volume of the undiluted dialysate solution to be additionally prepared (dissolved) varies with whether there are any courses remaining.

The present teachings have been conceived in view of the above circumstances and provides a blood purification system and a solution-preparation-determining apparatus with which the determination of whether additional preparation of an undiluted dialysate solution is necessary is achieved accurately.

According to variation 1, there is provided a blood purification system including a solution-preparing unit that prepares an undiluted dialysate solution, a dialysate-supplying unit that prepares a working dialysate at a predetermined concentration by diluting the undiluted dialysate solution received from the solution-preparing unit, a blood-purification-treatment section that includes a blood-purification-apparatus group including at least one blood purification apparatus that performs blood purification treatment in which the working dialysate prepared by the dialysate-supplying unit is supplied to the blood-purification-apparatus group, and a determining unit that determines whether additional preparation of the undiluted dialysate solution by the solution-preparing unit is necessary from a result of comparison between an estimated number of treatment sessions expected to be performed by the blood-purification-apparatus group throughout a predetermined period and an actual number of treatment sessions performed by the blood-purification-apparatus group as of a time point during the predetermined period.

According variation 2, in the blood purification system according to variation 1, the solution-preparing unit includes a control unit that operates such that the undiluted dialysate solution is prepared through dissolution of the drug if it is determined by the determining unit that additional preparation of the undiluted dialysate solution is necessary.

According to variation 3, in the blood purification system according to variation 1 or 2, the determining unit determines whether additional preparation of the undiluted dialysate solution is necessary by comparing the actual number of treatment sessions and the estimated number of treatment sessions of the blood purification treatment that is performed throughout a calendar day or a treatment hour regarded as the predetermined period.

According to variation 4, in the blood purification system according to any of variations 1 to 3, the blood purification apparatus includes a transmitting unit that transmits the actual number of treatment sessions to the determining unit.

According to variation 5, in the blood purification system according to variation 4, the transmitting unit of the blood purification apparatus transmits start or end of the blood purification treatment or an hour of the blood purification treatment to the determining unit.

According to variation 6, in the blood purification system according to any of variations 1 to 5, the determining unit determines whether any shortage of the undiluted dialysate solution in the solution-preparing unit is expected to occur during a current treatment session, in addition to determining whether additional preparation is necessary from the actual number of treatment sessions and the estimated number of treatment sessions.

According to variation 7, in the blood purification system according to variation 6, the determining unit estimates a volume of the undiluted dialysate solution expected to be consumed throughout a specific treatment hour from a volume, flow velocity, and hour or time of supply of the working dialysate received by the blood purification apparatus or from step information or treatment suspension information regarding the blood purification apparatus. Furthermore, the determining unit determines whether any shortage of the undiluted dialysate solution in the solution-preparing unit is expected to occur, by comparing the estimated volume of the undiluted dialysate solution expected to be consumed and a volume of the undiluted dialysate solution remaining in the solution-preparing unit.

According to variation 8, in the blood purification system according to any of variations 1 to 7, the estimated number of treatment sessions is set with reference to past treatment data or treatment-reservation data.

According to variation 9, there is provided a blood purification system including a solution-preparing unit that prepares an undiluted dialysate solution, a blood-purification-treatment section that includes a blood-purification-apparatus group including at least one blood purification apparatus that performs blood purification treatment in which the undiluted dialysate solution prepared by the solution-preparing unit is supplied to the blood-purification-apparatus group, and a determining unit that determines whether additional preparation of the undiluted dialysate solution by the solution-preparing unit is necessary from a result of comparison between an estimated number of treatment sessions expected to be performed by the blood-purification-apparatus group throughout a predetermined period and an actual number of treatment sessions performed by the blood-purification-apparatus group as of a time point during the predetermined period.

According to variation 10, there is provided a solution-preparation-determining apparatus connected to and capable of communicating with a blood-purification-apparatus group including at least one blood purification apparatus to which a working dialysate is supplied for blood purification treatment, the solution-preparation-determining apparatus serving as a dialysate-supplying apparatus that supplies the working dialysate to the blood-purification-apparatus group or as a solution-preparing apparatus that prepares an undiluted dialysate solution for the supply of the working dialysate. The solution-preparation-determining apparatus includes a determining unit that determines whether additional preparation of the undiluted dialysate solution by the solution-preparing unit is necessary from a result of comparison between an estimated number of treatment sessions expected to be performed by the blood-purification-apparatus group throughout a predetermined period and an actual number of treatment sessions performed by the blood-purification-apparatus group as of a time point during the predetermined period.

According to each of variations 1, 9, and 10, whether additional preparation of the undiluted dialysate solution by the solution-preparing unit is necessary is determined from the result of comparison between the estimated number of treatment sessions expected to be performed by the blood-purification-apparatus group throughout the predetermined period and the actual number of treatment sessions performed by the blood-purification-apparatus group as of a time point during the predetermined period. Therefore, the determination of whether additional preparation of the undiluted dialysate solution is necessary is achieved accurately.

According to variation 2, the solution-preparing unit includes the control unit that operates such that the undiluted dialysate solution is prepared through the dissolution of the drug if it is determined by the determining unit that additional preparation of the undiluted dialysate solution is necessary. Therefore, additional preparation of the undiluted dialysate solution is achieved with consideration for the time taken to dissolve the drug.

According to variation 3, the determining unit determines whether additional preparation of the undiluted dialysate solution is necessary by comparing the actual number of treatment sessions and the estimated number of treatment sessions of the blood purification treatment that is performed throughout the calendar day or the treatment hour regarded as the predetermined period. Therefore, the determination of whether additional preparation of the undiluted dialysate solution is necessary is made throughout the specific calendar day or the specific treatment hour.

According to variation 4, the blood purification apparatus includes the transmitting unit that transmits the actual number of treatment sessions to the determining unit. Therefore, the determination of whether additional preparation of the undiluted dialysate solution is necessary is achieved quickly and smoothly by the determining unit.

According to variation 5, the transmitting unit of the blood purification apparatus transmits the start or end of the blood purification treatment or the hour of the blood purification treatment to the determining unit. Therefore, the actual number of treatment sessions is identified accurately.

According to variation 6, the determining unit determines whether any shortage of the undiluted dialysate solution in the solution-preparing unit is expected to occur during the current treatment session, in addition to determining whether additional preparation is necessary from the actual number of treatment sessions and the estimated number of treatment sessions. Therefore, the determination of whether additional preparation is necessary in the current treatment session is achieved smoothly.

According to variation 7, the determining unit estimates the volume of the undiluted dialysate solution expected to be consumed throughout the specific treatment hour from the volume, flow velocity, and hour or time of supply of the working dialysate received by the blood purification apparatus or from the step information or the treatment suspension information regarding the blood purification apparatus. Furthermore, the determining unit determines whether any shortage of the undiluted dialysate solution in the solution-preparing unit is expected to occur, by comparing the estimated volume of the undiluted dialysate solution expected to be consumed and the volume of the undiluted dialysate solution remaining in the solution-preparing unit. Therefore, the determination of whether additional preparation is necessary in the current treatment session is achieved more accurately and smoothly.

According to variation 8, the estimated number of treatment sessions is set with reference to the past treatment data or the treatment-reservation data. Therefore, the determination of whether additional preparation of the undiluted dialysate solution is necessary is achieved smoothly and accurately.

BRIEF DESCRIPTION OF THE DRAWINGS

FIG. 1 is a schematic diagram illustrating the entirety of a blood purification system according to an embodiment of the present teachings.

FIG. 2 is a schematic diagram illustrating the configuration of a dissolving apparatus included in the blood purification system.

FIG. 3 is a schematic diagram illustrating the configuration of a dialysate-supplying apparatus included in the blood purification system.

FIG. 4 is a schematic diagram illustrating the configuration of a dialysis monitoring apparatus included in the blood purification system.

FIG. 5 is a flow chart illustrating a method of determination made by a determining unit included in the blood purification system.

FIG. 6 is a schematic diagram illustrating the entirety of a blood purification system according to the present teachings.

FIG. 7 is a schematic diagram illustrating the entirety of a blood purification system according to the present teachings.

DETAILED DESCRIPTION

Embodiments of the present teachings will now be described specifically with reference to the drawings.

A blood purification system according to an embodiment is intended to prepare a working dialysate at a predetermined concentration from an undiluted dialysate solution and to supply the working dialysate to a plurality of dialysis monitor apparatuses (blood purification apparatuses). As illustrated in FIG. 1, the blood purification system basically includes a dissolving apparatus 1, which serves as a solution-preparing unit; a dialysate-supplying apparatus 2, which serves as a dialysate-supplying unit; and a blood-purification-treatment section including a plurality of dialysis monitoring apparatuses 3 (a blood-purification-apparatus group) installed in a dialysis room (a treatment room) provided in a medical site such as a hospital. The blood purification system according to the present embodiment may include a single dialysis monitoring apparatus 3 (a blood-purification-apparatus group), in replacement of the plurality of dialysis monitoring apparatuses 3.

The dissolving apparatus 1 and the dialysate-supplying apparatus 2 are connected to each other with a tube R1, which allows an A-solution and a B-solution, which are prepared by the dissolving apparatus 1, to be supplied to the dialysate-supplying apparatus 2. The dialysate-supplying apparatus 2 and the dialysis monitoring apparatuses 3 are connected to each other with a tube R2, which allows the working dialysate prepared by the dialysate-supplying apparatus 2 to be supplied to the dialysis monitoring apparatuses 3. Thus, the A-solution and the B-solution prepared by the dissolving apparatus 1 are made into a working dialysate by the dialysate-supplying apparatus 2, and the working dialysate is supplied to the dialysis monitoring apparatuses 3, with which dialysis treatment (blood purification treatment) is performed.

The dissolving apparatus 1 and the dialysate-supplying apparatus 2 are electrically connected to each other with a LAN cable C1, which allows the transmission and reception of information therebetween. The dialysate-supplying apparatus 2 and the dialysis monitoring apparatuses 3 are electrically connected to each other with a LAN cable C2, which allows the transmission and reception of information therebetween.

That is, in the blood purification system according to the present embodiment, the dissolving apparatus 1, the dialysate-supplying apparatus 2, and the dialysis monitoring apparatuses 3 are connected to one another over a LAN (local area network) so as to be capable of bidirectional communication of information. Hence, in the blood purification system, the plurality of dialysis monitoring apparatuses 3 are capable of individually transmitting predetermined information on themselves to the dialysate-supplying apparatus 2. The network is not limited to the one with LAN cables (a wired network) employed in the present embodiment and may be a network that enables bidirectional communication with no wires (a wireless LAN).

The dissolving apparatus 1 prepares the undiluted dialysate solution by dissolving a drug, stores the undiluted dialysate solution of a predetermined volume, and supplies the undiluted dialysate solution stored therein to the dialysate-supplying apparatus 2. As illustrated in FIG. 2, the dissolving apparatus 1 includes a dissolving tank Ta1, in which an A-drug is received from a container B1 and is dissolved; a tank Ta2, in which the A-solution thus obtained in the dissolving tank Ta1 is stored; a dissolving tank Tb1, in which a B-drug is received from a container B2 and is dissolved; and a tank Tb2, in which the B-solution thus obtained in the dissolving tank Tb1 is stored.

The tank Ta2 and the tank Tb2 are respectively provided with remaining volume sensors Sa1 and Sb1, which detect the surface levels of the solutions stored in the respective tanks Ta2 and Tb2 and thus determine the volumes of the respective solutions remaining therein. The tank Ta2 and the tank Tb2 are connected to the dissolving tank Ta1 and the dissolving tank Tb1, respectively. When electromagnetic valves Va1 and Vb1 are open, the A-solution in the dissolving tank Ta1 and the B-solution in the dissolving tank Tb1 are allowed to flow down into the tank Ta2 and the tank Tb2, respectively. The dissolving tank Ta1 and the dissolving tank Tb1 are provided thereinside with respective liquid-level sensors Sa2 and Sb2, which each detect the surface level at the lower limit; and respective liquid-level sensors Sa3 and Sb3, which each detect the surface level at the upper limit.

The container B1 and the container B2 are set at respective predetermined positions, and the distal ends of flow routes La1 and Lb1 and flow routes La2 and Lb2 are each placed inside a corresponding one of the containers B1 and B2. Then, clean water (RO water) of a predetermined volume is introduced into the dissolving apparatus 1 through a water-feeding route Lw and is fed into the dissolving tank Ta1 through a flow route Lwa, and clean water (RO water) of a predetermined volume is introduced into the dissolving tank Tb1 through a flow route Lwb. In this process, the electromagnetic valves Va1 and Vb1 are closed.

Subsequently, the water feeding is stopped, and pumps Pa1 and Pb1 are activated. Accordingly, the A-drug and the clean water are mixed together by being made to circulate between the dissolving tank Ta1 and the container B1, whereby the A-solution is obtained. On the other hand, the B-drug and the clean water are mixed together by being made to circulate between the dissolving tank Tb1 and the container B2, whereby the B-solution is obtained. The A-solution and the B-solution prepared as above have different compositions for obtaining respective working dialysates. Specifically, the A-solution (an undiluted solution of the A-drug) is a mixed aqueous solution containing sodium chloride, potassium chloride, calcium chloride, magnesium chloride, sodium acetate, and the like. The B-solution (an undiluted solution of the B-drug) is an aqueous solution of sodium hydrogen carbonate.

After the A-solution and the B-solution of predetermined volumes are prepared in the dissolving tank Ta1 and the dissolving tank Tb1, if the pump Pa1 is stopped and the electromagnetic valve Va1 is opened, the A-solution in the dissolving tank Ta1 is made to flow down into the tank Ta2 by its own weight and is stored therein. On the other hand, if the pump Pb1 is stopped and the electromagnetic valve Vb1 is opened, the B-solution in the dissolving tank Tb1 is made to flow down into the tank Tb2 by its own weight and is stored therein.

After the A-solution or the B-solution in the dissolving tank Ta1 or Tb1 is all made to flow down into the tank Ta2 or Tb2, the container B1 or B2 thus emptied is detached. Instead, a new container B1 or B2 containing the A-drug or the B-drug is set. By following the above, the A-solution and the B-solution of predetermined volumes are obtained in the respective dissolving tanks Ta1 and Tb1. Subsequently, if a pump Pa2 is activated, the A-solution in the tank Ta2 is supplied to the dialysate-supplying apparatus 2. On the other hand, if a pump Pb2 is activated, the B-solution in the tank Tb2 is supplied to the dialysate-supplying apparatus 2. In addition, if the electromagnetic valve Va2 is opened, the A-solution in the tank Ta2 is drained. If the electromagnetic valve Vb2 is opened, the B-solution in the tank Tb2 is drained.

The dissolving apparatus 1 according to the present embodiment further includes an interface unit 1a and a control unit 1b, which are each electrically connected to the LAN cable C1. The interface unit 1a is capable of transmitting and receiving predetermined information to and from an interface unit 2a, which is included in the dialysate-supplying apparatus 2. When the interface unit 1a receives the predetermined information from the dialysate-supplying apparatus 2, the control unit 1b executes a control sequence for a predetermined operation in accordance with the information.

The dialysate-supplying apparatus 2 prepares a working dialysate at a predetermined concentration by diluting the undiluted dialysate solution (the A-solution and the B-solution) received from the dissolving apparatus 1 (the solution-preparing unit) through the tube R1. As illustrated in FIG. 3, the dialysate-supplying apparatus 2 includes a measuring unit 5, undiluted-solution pumps Pa and Pb, and a dialysate tank 6. If the undiluted-solution pump Pa is activated, the A-solution prepared by the dissolving apparatus 1 is supplied into the dialysate tank 6. If the undiluted-solution pump Pb is activated, the B-solution prepared by the dissolving apparatus 1 is supplied into the dialysate tank 6. Furthermore, clean water (RO water) of a predetermined volume measured by the measuring unit 5 is supplied into the dialysate tank 6 and is mixed and stirred with the A-solution and the B-solution therein, whereby a working dialysate at a predetermined concentration is obtained.

The dialysate-supplying apparatus 2 according to the present embodiment includes the interface unit 2a and a control unit 2b, which are each electrically connected to the LAN cables C1 and C2. The interface unit 2a is capable of transmitting and receiving predetermined information to and from the interface unit 1a included in the dissolving apparatus 1 and to and from an interface unit 3b, which is included in each of the dialysis monitoring apparatuses 3. When the interface unit 2a receives the predetermined information from the dissolving apparatus 1 or the dialysis monitoring apparatuses 3, the control unit 2b executes a control sequence for a predetermined operation in accordance with the information.

The working dialysate prepared by the dialysate-supplying apparatus 2 is supplied to the dialysis monitoring apparatuses 3 through the tube R2. As illustrated in FIG. 4, each dialysis monitoring apparatus 3 (the blood purification apparatus) is provided with a dialyzer 9 (a blood purifier) for giving blood purification treatment (hemodialysis treatment) to a patient. The dialysis monitoring apparatus 3 is intended to supply the working dialysate received from the dialysate-supplying apparatus 2 to the dialyzer 9. The dialysis monitoring apparatus 3 includes a touch panel 3a, which is capable of displaying information on hemodialysis treatment, an instruction for a control sequence of another operation (cleaning or disinfection), and other pieces of predetermined information.

Specifically, as illustrated in FIG. 4, each of the plurality of dialysis monitoring apparatuses 3 includes a dialysate introduction line L1, which is connected to the tube R2 extending from the dialysate-supplying apparatus 2; a drain-liquid discharge line L2, which is connected to a drainage device, not illustrated; and a duplex pump 7, which is provided astride the dialysate introduction line L1 and the drain-liquid discharge line L2. The dialysate introduction line L1 is provided with sensors such as a flow-rate sensor that detects the flow rate of liquid flowing in the dialysate introduction line L1, a fluid-pressure sensor that detects the fluid pressure at which the liquid is supplied, and a conductivity sensor that detects the conductivity (concentration) of the liquid.

The dialyzer 9 (the blood purifier) houses a plurality of hollow fiber membranes (not illustrated) formed of hollow fibers, which serve as blood purification membranes for purifying the blood. The dialyzer 9 has, in a housing thereof, a blood inlet 9a, a blood outlet 9b, a dialysate inlet 9c, and a dialysate outlet 9d. The blood inlet 9a is connected to an arterial blood circuit La. The blood outlet 9b is connected to a venous blood circuit Lb. The dialysate inlet 9c and the dialysate outlet 9d are connected to the dialysate introduction line L1 and the drain-liquid discharge line L2, respectively.

While blood of the patient is caused to extracorporeally circulate through the arterial blood circuit La and the venous blood circuit Lb with the activation of a blood pump 10, the working dialysate is introduced into the dialyzer 9 with the activation of the duplex pump 7, whereby dialysis treatment (blood purification treatment) is achieved. The dialysis monitoring apparatus 3 further includes an ultrafiltration pump 8. When the ultrafiltration pump 8 is activated, the blood of the patient flowing in the dialyzer 9 is ultrafiltered. The duplex pump 7 may be replaced with a so-called chamber-type device.

The dialysis monitoring apparatus 3 according to the present embodiment includes the interface unit 3b (a transmitting unit) and a control unit 3c, which are each electrically connected to the LAN cable C2. The interface unit 3b is capable of transmitting and receiving predetermined information to and from the interface unit 2a included in the dialysate-supplying apparatus 2. When the interface unit 3b receives the predetermined information from the dialysate-supplying apparatus 2, the control unit 3c executes a control sequence for a predetermined operation in accordance with the information.

The blood purification system according to the present embodiment includes a determining unit 2c in the dialysate-supplying apparatus 2. The determining unit 2c determines whether additional preparation (refeeding) of the undiluted dialysate solution by the dissolving apparatus 1 (the solution-preparing unit) is necessary, by comparing the actual number of treatment sessions performed by the dialysis monitoring apparatuses 3 (the blood purification apparatuses) and the estimated number of treatment sessions expected to be performed by the dialysis monitoring apparatuses 3. If it is determined by the determining unit 2c that additional preparation of the undiluted dialysate solution (the A-solution and the B-solution) is necessary, the control unit 1b of the dissolving apparatus 1 according to the present embodiment operates such that the undiluted dialysate solution (the A-solution and the B-solution) is prepared through the dissolution of the drug contained in the container B1 or B2. The undiluted dialysate solution thus additionally prepared is supplied to the dialysate-supplying apparatus 2 with an appropriate timing.

Specifically, the dialysis monitoring apparatuses 3 (the blood purification apparatuses) each transmit information on the actual number of treatment sessions to the dialysate-supplying apparatus 2 through the LAN cable C2. Then, the determining unit 2c of the dialysate-supplying apparatus 2 compares the "actual number of treatment sessions" thus received and the "estimated number of treatment sessions", which is inputted thereto (stored therein) in advance, thereby determining whether additional preparation of the undiluted dialysate solution by the dissolving apparatus 1 is necessary. If it is determined by the determining unit 2c that additional preparation is necessary, a control signal is transmitted to the dissolving apparatus 1 through the LAN cable C1. In accordance with the control signal, the control unit 1b executes a control sequence, in which the A-drug and the B-drug received from the container B1, B2 is dissolved in the dissolving tank Ta1 or Tb1, whereby the A-solution and the B-solution is obtained.

In each of the dialysis monitoring apparatuses 3 according to the present embodiment, the interface unit 3b (the transmitting unit) transmits the start or end of the blood purification treatment (step information) or the hour of the blood purification treatment to the determining unit 2c of the dialysate-supplying apparatus 2. With reference to the "start or end of the blood purification treatment (step information) or the hour of the blood purification treatment", the determining unit 2c identifies the "actual number of treatment sessions" as of the current time point, for comparison with the "estimated number of treatment sessions". The term "actual number of treatment sessions" refers to the sum of the numbers of treatment sessions actually performed by the dialysis monitoring apparatuses 3: in other words, the actual number of treatment sessions performed in the blood purification system (the blood-purification-apparatus group). The term "estimated number of treatment sessions" refers to the sum of the numbers of treatment sessions expected to be performed by the dialysis monitoring apparatuses 3: in other words, the estimated number of treatment sessions expected to be performed in the blood purification system (the blood-purification-apparatus group). The "actual number of treatment sessions" and the "estimated number of treatment sessions" may not necessarily be counted for all of the dialysis monitoring apparatuses 3 included in the blood purification system and may be counted for only some of the dialysis monitoring apparatuses 3. The step information may be information indicating the progress of the blood purification treatment, in replacement of the start or end of the blood purification treatment.

The "estimated number of treatment sessions" according to the present embodiment is set with reference to past treatment data or treatment-reservation data. Past treatment data refers to information based on past records obtained in the medical facility of interest. For example, patients' treatment records or the number of treatment sessions on a specific date and time in the past are referred to for the calculation. The treatment-reservation data refers to information on the dates and times of treatment sessions reserved by patients. For example, details of reservations on a specific date and time in the future are referred to for the calculation. The estimated number of treatment sessions may be based on other pieces of data such as information inputted by an operator.

The determining unit 2c according to the present embodiment determines whether additional preparation of the undiluted dialysate solution (the A-solution and the B-solution) is necessary by comparing the actual number of treatment sessions and the estimated number of treatment sessions of the blood purification treatment that is performed throughout a specific calendar day (including a specific day of the week or the like) or a specific treatment hour (including the "course"). The specific date or the specific treatment hour is defined as a predetermined period, such as one day, half a day, or one course. The predetermined period is desirably set shorter than or equal to a period from when the dissolving apparatus 1 starts dissolution for the supply of the undiluted dialysate solution to the dialysis monitoring apparatuses 3 until the undiluted dialysate solution is disposed of in response to the ending (shutdown or standing by) of the blood purification system (the period or hour throughout which the dissolving apparatus 1 is in operation). The term "course" refers to a unit of the specific treatment hour that is predetermined in the medical site such as a hospital. Dialysis treatment is given to a plurality of patients in every course. For example, there may be a morning course, an afternoon course, and a night course in a day.

In addition to "determining whether additional preparation is necessary from the actual number of treatment sessions and the estimated number of treatment sessions" as described above, the determining unit 2c according to the present embodiment determines whether any shortage of the undiluted dialysate solution (the A-solution or the B-solution) in the dissolving apparatus 1 is expected to occur during the current treatment session. Specifically, the determining unit 2c estimates the volume of the undiluted dialysate solution (the A-solution and the B-solution) expected to be consumed throughout the specific treatment hour from the volume, flow velocity, and hour or time of supply of the working dialysate received by the dialysis monitoring apparatuses 3 (the blood purification apparatuses) or from step information (regarding a pre-treatment priming step, a gas-purging step, a hemodialysis treatment step, a blood return step, a cleaning/disinfecting step, a substitution step, or the like) or treatment suspension information regarding the dialysis monitoring apparatuses 3 (the blood purification apparatuses). Furthermore, the determining unit 2c determines whether any shortage of the undiluted dialysate solution in the dissolving apparatus 1 is expected to occur, by comparing the estimated volume of the undiluted dialysate solution expected to be consumed and the volume of the undiluted dialysate solution remaining in the dissolving apparatus 1 (in the present embodiment, the sum of the volume of the undiluted dialysate solution remaining in the dissolving tank Ta1 or Tb1 and the volume of the undiluted dialysate solution remaining in the tank Ta2 or Tb2).

Now, a method of determination made by the determining unit 2c of the blood purification system according to the present embodiment will be described with reference to the flow chart illustrated in FIG. 5.

First, in S1, one of the undiluted solutions (the A-solution and the B-solution) is selected, and whether the remaining volume of the selected one of the A-solution and the B-solution is enough is determined. Specifically, the driving speeds of the undiluted-solution pumps Pa and Pb included in the dialysate-supplying apparatus 2 are adjusted in accordance with the desired composition of the solution to be obtained. Therefore, the time taken for the undiluted solution to be consumed may not necessarily be the same between the A-solution and the B-solution. Hence, one of the solutions (the A-solution and the B-solution) that is expected to be consumed in a shorter time is selected. This selection of one of the undiluted solutions is done every time the determination of whether additional preparation (additional dissolution) is necessary is made.

The undiluted solution to be selected is determined with reference to the capacity and the estimated volume of consumption divided by the estimated speed of consumption for each of the A-solution and the B-solution. The estimated speed of consumption is calculable from, for example, the driving speed of a corresponding one of the undiluted-solution pumps Pa and Pb included in the dialysate-supplying apparatus 2. Specifically, which of the A-solution and the B-solution is to be selected is calculable in accordance with the following expressions.

First, in accordance with Expressions (3) and (4) below, a length of time (time elapsed from a reference time) Ta taken for the A-solution of the estimated volume to be completely consumed and a length of time (time elapsed from the reference time) Tb taken for the B-solution of the estimated volume to be completely consumed are calculated.

$$X = \alpha_1 - \alpha_2 \times Ta \quad (1)$$

$$Y = \beta_1 - \beta_2 \times Tb \quad (2)$$

If X=0 in Expression (1) (if the A-solution of the estimated volume is completely consumed), $$Ta = \alpha_1 / \alpha_2 \quad (3)$$

If Y=0 in Expression (2) (if the B-solution of the estimated volume is completely consumed), $$Tb = \beta_1 / \beta_2 \quad (4)$$

(In the above expressions, $\alpha_1$ denotes the volume of the A-solution, $\beta_1$ denotes the volume of the B-solution, $\alpha_2$ (an absolute value) denotes the estimated speed of consumption of the A-solution, $\beta_2$ (an absolute value) denotes the estimated speed of consumption of the B-solution, X denotes the estimated volume of the A-solution after time Ta has elapsed, and Y denotes the estimated volume of the B-solution after time Tb has elapsed).

The length of time Ta taken for the A-solution of the estimated volume to be completely consumed and the length of time Tb taken for the B-solution of the estimated volume to be completely consumed are compared. If Ta is greater than Tb, the B-solution is selected. If Ta is smaller than Tb, the A-solution is selected. If Ta and Tb are equal, the A-solution is selected.

After one of the undiluted solutions is selected in S1, the sequence proceeds to S2, in which whether the remaining volume of the undiluted solution is enough is determined. Specifically, S2 is intended to determine whether any shortage of the undiluted dialysate solution (the A-solution or the B-solution) in the dissolving apparatus 1 (the solution-preparing unit) is expected to occur during the current treatment session. Specifically, the determination of whether any shortage of the undiluted dialysate solution is expected to occur is made under the following conditions.

Let the remaining volume of the A-solution or the B-solution in the dissolving apparatus 1 (for the A-solution, the sum of the volumes remaining in the dissolving tank Ta1 and the tank Ta2; for the B-solution, the sum of the volumes remaining in the dissolving tank Tb1 and the tank Tb2) be X(L), the margin be Y(L), and the cumulative volume of consumption of the undiluted solution at a future time point that is estimated at the current time be Z(L). If the result of a calculation (X−Y)−Z is 0 or greater, it is determined that the remaining volume of the undiluted solution is enough. If the result of the calculation (X−Y)−Z is smaller than 0, it is determined that the remaining volume of the undiluted solution is short.

If it is determined in S2 that the remaining volume of the undiluted solution is enough, the sequence proceeds to S3, in which the actual number of treatment sessions performed by the dialysis monitoring apparatuses 3 and the estimated number of treatment sessions expected to be performed by the dialysis monitoring apparatuses 3 are compared to determine whether additional preparation of the undiluted dialysate solution (the A-solution or the B-solution) by the dissolving apparatus 1 is necessary. If only one course of dialysis treatment is performed in the medial facility of interest, only the determination in S2 will do. However, in some medial facilities or on some days of the week, there may be a plurality of courses. In such a case, whether there are any courses remaining needs to be identified. If whether there are any courses remaining is not identified, the undiluted dialysate solution (the A-solution or the B-solution) of an unexpectedly large volume may be necessary at the start of the subsequent course (for example, when priming is started in a plurality of apparatuses at a time), leading to the exhaustion of the undiluted dialysate solution in the dissolving apparatus 1. Therefore, in the present embodiment, whether there are any treatment sessions (courses) remaining is identified, with reference to which the determination for additional preparation is made.

Specifically, the determining unit 2c first receives history data (past treatment data) regarding the number of treatment sessions performed on a day of the week of interest. Furthermore, the determining unit 2c periodically receives information on the number of treatment sessions on the current day, and calculates the difference from the history data (the past treatment data). If the difference is over a threshold, it is determined that there are treatment sessions remaining. Even if it is determined in S2 that the remaining volume of the undiluted solution is enough, additional preparation is executed if there are any treatment sessions remaining. In the present embodiment, additional preparation is executed under the following conditions.

Let the remaining volume of the A-solution or the B-solution in the dissolving apparatus 1 (for the A-solution, the sum of the volumes remaining in the dissolving tank Ta1 and the tank Ta2; for the B-solution, the sum of the volumes remaining in the dissolving tank Tb1 and the tank Tb2) be $X(L)$, the margin be $Y(L)$, the cumulative volume of consumption of the undiluted solution at a future time point that is estimated at the current time be $Z(L)$, and the volume of the undiluted solution that is consumed per dialysis monitoring apparatus throughout a time period taken for the dissolving apparatus 1 to prepare the undiluted solution be $Q(L)$. If the result of a calculation $\{(X-Y)-Z\}-Q \times$ the number of treatment sessions remaining is 0 or greater, it is determined that additional preparation is not necessary. If the result of the calculation $\{(X-Y)-Z\}-Q \times$ the number of treatment sessions remaining is smaller than 0, it is determined that additional preparation is necessary.

Subsequently, if it is determined in S3 that additional preparation is necessary, whether the dissolving apparatus 1 is ready for additional preparation (dissolution) is determined in S4. If it is determined that the dissolving apparatus 1 is ready, additional preparation is executed in S5. If it is determined in S2 that the remaining volume of the undiluted solution is not enough, S3 is skipped and the sequence proceeds to S4. If it is determined in S3 or S4 that additional preparation is not necessary or that the dissolving apparatus 1 is not ready for additional preparation, the sequence proceeds to S6 for standby and then returns to S1.

According to the above embodiment, whether additional preparation of the undiluted dialysate solution by the dissolving apparatus 1 (the solution-preparing unit) is necessary is determined from the result of comparison between the estimated number of treatment sessions expected to be performed by the blood-purification-apparatus group throughout a predetermined period and the actual number of treatment sessions performed by the blood-purification-apparatus group as of a time point during the predetermined period. Therefore, the determination of whether additional preparation of the undiluted dialysate solution is necessary is achieved accurately.

The dissolving apparatus 1 (the solution-preparing unit) according to the present embodiment prepares the undiluted dialysate solution (the A-solution and the B-solution) by dissolving the drug (the A-drug and the B-drug) and stores the undiluted dialysate solution (the A-solution and the B-solution) of a predetermined volume. Furthermore, the dissolving apparatus 1 (the solution-preparing unit) includes the control unit 1$b$ that operates such that the undiluted dialysate solution is prepared through the dissolution of the drug if it is determined by the determining unit 2$c$ that additional preparation of the undiluted dialysate solution is necessary. Therefore, additional preparation of the undiluted dialysate solution is achieved with consideration for the time taken to dissolve the drug.

Furthermore, the determining unit 2$c$ according to the present embodiment determines whether additional preparation of the undiluted dialysate solution is necessary by comparing the actual number of treatment sessions and the estimated number of treatment sessions of the blood purification treatment that is performed throughout a calendar day or a treatment hour regarded as the predetermined period. Therefore, the determination of whether additional preparation of the undiluted dialysate solution is necessary is made throughout the specific calendar day or the specific treatment hour. In the present embodiment, the estimated number of treatment sessions is set with reference to the past treatment data or the treatment-reservation data. Therefore, the determination of whether additional preparation of the undiluted dialysate solution is necessary is achieved smoothly and accurately.

The dialysis monitoring apparatuses 3 according to the present embodiment each include the transmitting unit (the interface unit 3$b$) that transmits the actual number of treatment sessions to the determining unit 2$c$. Therefore, the determination of whether additional preparation of the undiluted dialysate solution is necessary is achieved quickly and smoothly by the determining unit 2$c$. The transmitting unit (the interface unit 3$b$) of each of the dialysis monitoring apparatuses 3 (the blood purification apparatuses) according to the present embodiment transmits the start or end of the blood purification treatment or the hour of the blood purification treatment to the determining unit. Therefore, the actual number of treatment sessions is identified accurately.

The determining unit 2$c$ according to the present embodiment determines whether any shortage of the undiluted dialysate solution in the dissolving apparatus 1 (the solution-preparing unit) is expected to occur during the current treatment session, in addition to determining whether additional preparation is necessary from the actual number of treatment sessions and the estimated number of treatment sessions. Therefore, the determination of whether additional preparation of the undiluted dialysate solution is necessary in the current treatment session is achieved smoothly.

In particular, the determining unit 2$c$ according to the present embodiment estimates the volume of the undiluted dialysate solution expected to be consumed throughout the specific treatment hour from the volume, flow velocity, and hour or time of supply of the working dialysate received by the dialysis monitoring apparatuses 3 (the blood purification apparatuses) or from step information or treatment suspension information regarding the dialysis monitoring apparatuses 3 (the blood purification apparatuses). Furthermore, the determining unit 2$c$ determines whether any shortage of the undiluted dialysate solution in the dissolving apparatus 1 (the solution-preparing unit) is expected to occur, by comparing the estimated volume of the undiluted dialysate solution expected to be consumed and the volume of the undiluted dialysate solution remaining in the dissolving apparatus 1. Therefore, the determination of whether additional preparation of the undiluted dialysate solution is necessary in the current treatment session is achieved more accurately and smoothly.

While the blood purification system according to the embodiment has been described above, the present invention is not limited thereto. For example, as illustrated in FIG. 6, a dialysis communication system 11 may be electrically connected to the dialysate-supplying apparatus 2 with a LAN cable C3, so that the estimated number of treatment sessions (the past treatment data or the treatment-reservation data) is transmitted from the dialysis communication system 11 to the determining unit 2$c$.

The determining unit 2$c$ is not limited to the one included in the dialysate-supplying apparatus 2 and may be included in, for example, the dissolving apparatus 1 or another apparatus such as a computer. The dissolving apparatus 1 according to the present embodiment prepares the undiluted dialysate solution (the A-solution and the B-solution) by dissolving the drug (the A-drug and the B-drug) and stores the undiluted dialysate solution of a predetermined volume. Alternatively, the dissolving apparatus 1 may be a solution-preparing unit of another type that stores the undiluted dialysate solution (the A-solution and the B-solution) of a predetermined volume and supplies the undiluted dialysate solution to the dialysate-supplying apparatus 2. The dissolving apparatus 1 according to the present embodiment selects one of the undiluted solutions (the A-solution and the B-solution) and determines whether the remaining volume of the selected one of the A-solution and the B-solution is enough. If the A-solution and the B-solution are dissolvable individually, the determination of whether the remaining volume is enough may be made for the individual solutions, and additional preparation may be executed for the individual solutions.

In the blood purification system according to the present embodiment, the dissolving apparatus 1 and the dialysate-supplying apparatus 2 are separate from each other. Alternatively, the dissolving apparatus 1 and the dialysate-supplying apparatus 2 may be integrated into one apparatus. For example, as illustrated in FIG. 7, a blood purification system includes a dissolving apparatus 1' (a solution-preparing unit) that prepares an undiluted dialysate solution, a blood-purification-treatment section 4 that includes a blood-purification-apparatus group including at least one personal monitoring apparatus 3' (a blood purification apparatus) that performs blood purification treatment (hemodialysis treatment) in which the undiluted dialysate solution prepared by the dissolving apparatus 1' (the solution-preparing unit) is supplied to the blood-purification-apparatus group, and a determining unit that determines whether additional preparation of the undiluted dialysate solution by the dissolving apparatus 1' (the solution-preparing unit) is necessary from the result of comparison between the estimated number of treatment sessions expected to be performed by the blood-purification-apparatus group throughout a predetermined period and the actual number of treatment sessions performed by the blood-purification-apparatus group as of a time point during the predetermined period. Elements that are the same as those described in the above embodiment are denoted by corresponding ones of the reference signs, and detailed description of those elements is omitted.

The dissolving apparatus 1', which serves as a solution-preparing unit, prepares the undiluted dialysate solution (the A-solution and the B-solution) by dissolving a drug, stores the undiluted dialysate solution of a predetermined volume, and supplies the undiluted dialysate solution thus stored to personal monitoring apparatuses 3' through a tube R. The dissolving apparatus 1' includes an interface unit 2a, a control unit 2b, and a determining unit 2c. The interface unit 2a is capable of transmitting and receiving predetermined information to and from an interface unit 3b included in each of the personal monitoring apparatuses 3' through a LAN cable C. When the interface unit 2a receives the predetermined information from the personal monitoring apparatuses 3', the control unit 2b executes a control sequence for a predetermined operation in accordance with the information.

The plurality of personal monitoring apparatuses 3' each include the interface unit 3b (a transmitting unit) and a control unit 3c, which are each electrically connected to the LAN cable C, as with the case of the above embodiment. The interface unit 3b is capable of transmitting and receiving predetermined information to and from the interface unit 2a included in the dissolving apparatus 1'. When the interface unit 3b receives the predetermined information from the dissolving apparatus 1', the control unit 3c executes a control sequence for a predetermined operation in accordance with the information.

In particular, the personal monitoring apparatuses 3' are each capable of preparing a working dialysate at a predetermined concentration by diluting the undiluted dialysate solution (the A-solution and the B-solution) received from the dissolving apparatus 1' with clean water such as RO water. The working dialysate thus prepared is used for dialysis treatment (blood purification treatment). The dissolving apparatus 1' includes the determining unit 2c that determines whether additional preparation (refeeding) of the undiluted dialysate solution by the dissolving apparatus 1' (the solution-preparing unit) is necessary, by comparing the actual number of treatment sessions performed by the personal monitoring apparatuses 3' (the blood purification apparatuses) and the estimated number of treatment sessions expected to be performed by the personal monitoring apparatuses 3'. If it is determined by the determining unit 2c that additional preparation of the undiluted dialysate solution (the A-solution and the B-solution) is necessary, the control unit 2b of the dissolving apparatus 1' according to the present embodiment operates such that the undiluted dialysate solution (the A-solution and the B-solution) is prepared through the dissolution of the drug.

Specifically, information on the actual number of treatment sessions is transmitted from the personal monitoring apparatuses 3' (the blood purification apparatuses) to the dissolving apparatus 1' through the LAN cable C. The determining unit 2c of the dissolving apparatus 1' compares the "actual number of treatment sessions" received and the "estimated number of treatment sessions" inputted thereto (stored therein) in advance, thereby determining whether additional preparation of the undiluted dialysate solution is necessary. If it is determined by the determining unit 2c that additional preparation is necessary, the A-drug and the B-drug is dissolved, whereby the A-solution and the B-solution is obtained.

In the present embodiment, the information is transmitted through the LAN cable bidirectionally. Alternatively, bidirectional communication is not necessary if, for example, the information on the actual number of treatment sessions is transmittable from each of the dialysis monitoring apparatuses 3 to the determining unit 2c. The determining unit 2c according to the present embodiment determines whether any shortage of the undiluted dialysate solution in the solution-preparing unit is expected to occur during the current treatment session (S2 in FIG. 5), in addition to determining whether additional preparation is necessary from the actual number of treatment sessions and the estimated number of treatment sessions (S3 in FIG. 5). Alternatively, the determining unit 2c may only determine whether additional preparation is necessary from the actual number of treatment sessions and the estimated number of treatment sessions (S3 in FIG. 5), without determining whether any shortage of the undiluted dialysate solution in the solution-preparing unit is expected to occur during the current treatment session (S2 in FIG. 5). Moreover, whether to make the decision of whether additional preparation is necessary from the actual number of treatment sessions and the estimated number of treatment sessions (S3 in FIG. 5) may be determined from whether there are any courses (treatment sessions) currently remaining for the blood purification system (the blood-purification-apparatus group). Specifically, if there are any courses (treatment sessions) remaining, whether additional preparation is necessary is determined. If there are no courses (treatment sessions) remaining, the determination of whether additional preparation is necessary is skipped to increase control efficiency. The present embodiment relates to a system intended for dialysis treatment. Alternatively, the present invention may be applied to a blood purification system intended for another blood purification treatment.

In the present embodiment, whether additional preparation is necessary is determined by comparing the sum of the numbers of treatment sessions actually performed by the dialysis monitoring apparatuses 3 and the sum of the numbers of treatment sessions expected to be performed by the dialysis monitoring apparatuses 3. Another embodiment may be employed in which whether additional preparation is necessary is determined by comparing the number of courses actually undergone by the blood purification system (the blood-purification-apparatus group) and the number of courses expected to undergo by the blood purification system (the blood-purification-apparatus group). Note that in some medical sites such as hospitals, there may be no courses described above, and dialysis treatment is given to patients consecutively as they visit the treatment room. In such a case, for example, whether any shortage of the undiluted dialysate solution is expected to occur is not determined on the basis of courses that are set on the current day. In this respect, the blood purification system and the solution-preparation-determining apparatus according to the present embodiment are applicable to those medical sites such as hospitals that do not employ courses and are more advantageous than the other embodiment described above, because whether any shortage of the undiluted dialysate solution is expected to occur is determined from the actual number of treatment sessions and the estimated number of treatment sessions on the current day.

The present teachings are applicable to a blood purification system and a solution-preparation-determining apparatus with additional functions or the like, as long as the system and the apparatus each include a solution-preparing unit that prepares an undiluted dialysate solution, a dialysate-supplying unit that prepares a working dialysate at a predetermined concentration by diluting the undiluted dialysate solution received from the solution-preparing unit, a blood-purification-treatment section that includes a blood-purification-apparatus group including at least one blood purification apparatus that performs blood purification treatment in which the working dialysate prepared by the dialysate-supplying unit is supplied to the blood-purification-apparatus group, and a determining unit that determines whether additional preparation of the undiluted dialysate solution by the solution-preparing unit is necessary from the result of comparison between the estimated number of treatment sessions expected to be performed by the blood-purification-apparatus group throughout a predetermined period and the actual number of treatment sessions performed by the blood-purification-apparatus group as of a time point during the predetermined period.

REFERENCE SIGN LIST 1, 1' dissolving apparatus (solution-preparing unit)
1a interface unit
1b control unit
2 dialysate-supplying apparatus (dialysate-supplying unit)
2a interface unit
2b control unit
2c determining unit
3 dialysis monitoring apparatus (blood purification apparatus)
3a touch panel (display) (input unit)
3b interface unit (transmitting unit)
3c control unit
3' personal monitoring apparatus (blood purification apparatus)
4 blood-purification-treatment section
5 measuring unit
6 dialysate tank
7 duplex pump
8 ultrafiltration pump
9 dialyzer (blood purifier)
10 blood pump
11 dialysis communication system

The invention claimed is:

1. A blood purification system comprising:
a solution-preparing unit that prepares an undiluted dialysate solution;
a dialysate-supplying unit that prepares a working dialysate at a predetermined concentration by diluting the undiluted dialysate solution received from the solution-preparing unit and supplies the working dialysate;
a blood-purification-treatment section that includes a blood-purification-apparatus group including at least one blood purification apparatus that performs blood purification treatment in which the working dialysate prepared by the dialysate-supplying unit is supplied from the dialysate-supplying unit to the blood-purification-apparatus group; and
a determining unit that executes a first determining step of determining whether additional preparation of the undiluted dialysate solution by the solution-preparing unit is necessary from a number of remaining treatment sessions that is obtained as a result of comparison between an estimated number of treatment sessions expected to be performed by the blood-purification-apparatus group throughout a predetermined period and an actual number of treatment sessions performed by the blood-purification-apparatus group as of a time point during the predetermined period.

2. The blood purification system according to claim 1, wherein the solution-preparing unit includes a control unit that operates such that the undiluted dialysate solution is prepared through dissolution of a drug if it is determined by the determining unit that additional preparation of the undiluted dialysate solution is necessary.

3. The blood purification system according to claim 1, wherein the determining unit determines whether additional preparation of the undiluted dialysate solution is necessary by comparing the actual number of treatment sessions and the estimated number of treatment sessions of the blood purification treatment that is performed throughout a calendar day or a treatment hour regarded as the predetermined period.

4. The blood purification system according to claim 1, wherein the blood purification apparatus includes a transmitting unit that transmits the actual number of treatment sessions to the determining unit.

5. The blood purification system according to claim 4, wherein the transmitting unit of the blood purification apparatus transmits start or end of the blood purification treatment or an hour of the blood purification treatment to the determining unit.

6. The blood purification system according to claim 1, wherein the determining unit executes a second determining step of determining whether any shortage of the undiluted dialysate solution in the solution-preparing unit is expected to occur during a current treatment session, in addition to the first determining step of determining whether additional preparation is necessary from the number of remaining treatment sessions that is obtained as the result of comparison between the actual number of treatment sessions and the estimated number of treatment sessions.

7. The blood purification system according to claim 6, wherein the determining unit executes the second determining step and the first determining step in that order; and if it is determined by the determining unit in the second determining step that a shortage of the undiluted dialysate solution is expected to occur, the solution-preparing unit prepares the undiluted dialysate solution without the execution of the first determining step by the determining unit.

8. The blood purification system according to claim 6, wherein if it is determined by the determining unit in the second determining step that no shortage of the undiluted dialysate solution is expected to occur but it is determined by the determining unit in the first determining step that additional preparation is necessary, the solution-preparing unit prepares the undiluted dialysate solution.

9. The blood purification system according to claim 6, wherein the determining unit estimates a volume of the undiluted dialysate solution expected to be consumed throughout a specific treatment hour from a volume, flow velocity, and hour or time of supply of the working dialysate received by the blood purification apparatus or from step information or treatment suspension information regarding the blood purification apparatus; and the determining unit determines whether any shortage of the undiluted dialysate solution in the solution-preparing unit is expected to occur, by comparing the estimated volume of the undiluted dialysate solution expected to be consumed and a volume of the undiluted dialysate solution remaining in the solution-preparing unit.

10. The blood purification system according to claim 1, wherein the estimated number of treatment sessions is set with reference to past treatment data or treatment-reservation data.

11. A blood purification system comprising:
   a solution-preparing unit that prepares an undiluted dialysate solution;
   a blood-purification-treatment section that includes a blood-purification-apparatus group including at least one blood purification apparatus that performs blood purification treatment in which the undiluted dialysate solution prepared by the solution-preparing unit is supplied to the blood-purification-apparatus group; and
   a determining unit that determines whether additional preparation of the undiluted dialysate solution by the solution-preparing unit is necessary from a number of remaining treatment sessions that is obtained as a result of comparison between an estimated number of treatment sessions expected to be performed by the blood-purification-apparatus group throughout a predetermined period and an actual number of treatment sessions performed by the blood-purification-apparatus group as of a time point during the predetermined period.

12. A solution-preparation-determining apparatus connected to and capable of communicating with a blood-purification-apparatus group including at least one blood purification apparatus to which a working dialysate is supplied for blood purification treatment, the solution-preparation-determining apparatus serving as a dialysate-supplying apparatus that supplies the working dialysate to the blood-purification-apparatus group or as a solution-preparing apparatus that prepares an undiluted dialysate solution for the supply of the working dialysate, the solution-preparation-determining apparatus comprising:
   a determining unit that determines whether additional preparation of the undiluted dialysate solution by a solution-preparing unit is necessary from a number of remaining treatment sessions that is obtained as a result of comparison between an estimated number of treatment sessions expected to be performed by the blood-purification-apparatus group throughout a predetermined period and an actual number of treatment sessions performed by the blood-purification-apparatus group as of a time point during the predetermined period.

* * * * *